(12) United States Patent
Losada et al.

(10) Patent No.: US 7,030,250 B2
(45) Date of Patent: Apr. 18, 2006

(54) PROCESS FOR OBTAINING 4-(N-ALKYLAMINO)-5,6-DIHYDRO-4H-THIEN- (2,3-B)-THIOPYRAN-2-SULFONAMIDE-7,7-DIOXIDES AND INTERMEDIATES

(75) Inventors: Pablo García Losada, Boecillo (ES); Luis Octavio Silva Guisasola, Boecillo (ES); Antonio Lorente Bonde-Larsen, Boecillo (ES); Jorge Martín Juárez, Boecillo (ES)

(73) Assignee: Ragatives, S.L., Boecillo (ES)

( * ) Notice: Subject to any disclaimer, the term of this patent is extended or adjusted under 35 U.S.C. 154(b) by 212 days.

(21) Appl. No.: 10/379,096

(22) Filed: Mar. 3, 2003

(65) Prior Publication Data

US 2003/0220509 A1 Nov. 27, 2003

Related U.S. Application Data

(63) Continuation of application No. PCT/ES01/00335, filed on Sep. 4, 2001.

(30) Foreign Application Priority Data

Sep. 4, 2000 (ES) ................................ 200002171

(51) Int. Cl.
   *C07D 335/04* (2006.01)
(52) U.S. Cl. ...................................................... 549/23
(58) Field of Classification Search .................. 549/23
   See application file for complete search history.

(56) References Cited

U.S. PATENT DOCUMENTS

| 4,677,115 A | 6/1987 | Baldwin et al. |
| 4,797,413 A | 1/1989 | Baldwin et al. |
| 4,820,848 A | 4/1989 | Ponticello et al. |
| 4,824,968 A | 4/1989 | Ponticello et al. |
| 4,863,922 A | 9/1989 | Baldwin et al. |
| 5,091,409 A * | 2/1992 | Baldwin et al. ............ 514/434 |
| 5,120,757 A * | 6/1992 | Baldwin et al. ............ 514/432 |
| 5,391,772 A | 2/1995 | Thompson et al. |
| 5,441,722 A * | 8/1995 | Eng et al. .................. 424/1.11 |
| 5,474,919 A | 12/1995 | Chartrain et al. |
| 5,688,968 A * | 11/1997 | Blacklock et al. ............ 549/23 |
| 5,760,249 A | 6/1998 | Mathre et al. |

FOREIGN PATENT DOCUMENTS

| EP | 0 411 704 A1 | 7/1990 |
| EP | 0 452 151 A1 | 4/1991 |
| EP | 0 457 586 A1 | 5/1991 |
| EP | 0 590 549 A1 | 9/1993 |
| EP | 0 617 037 A1 | 3/1994 |
| WO | WO 94/05802 A1 | 3/1994 |

* cited by examiner

*Primary Examiner*—Deborah C. Lambkin
(74) *Attorney, Agent, or Firm*—Akin Gump Strauss Hauer & Feld, LLP

(57) ABSTRACT

The process for obtaining 4-(N-alkylamino)-5,6-dihydro-4H-thien-(2,3-b)-thiopyran-2-sulfonamide-7,7-dioxides (I) wherein $R_1$ is H or $C_{1-5}$ alkyl, and $R_2$ is $C_{1-5}$ alkyl, starts from the corresponding 4-(N-alkylamino)-5,6-dihydro-4H-thien-(2,3-b)-thiopyran-7,7-dioxides, and comprises protecting the alkylamine group, introducing a sulfonamide group and eliminating protecting group. Some compounds of formula (I) are inhibitors of the carbonic anhydrase and can be used in the treatment of elevated intraocular pressure

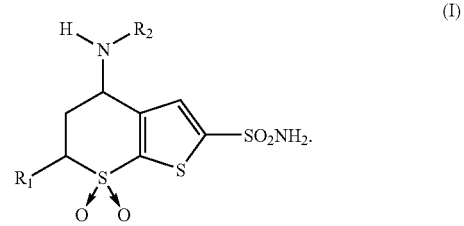

29 Claims, No Drawings

PROCESS FOR OBTAINING 4-(N-ALKYLAMINO)-5,6-DIHYDRO-4H-THIEN-(2,3-B)-THIOPYRAN-2-SULFONAMIDE-7,7-DIOXIDES AND INTERMEDIATES

CROSS-REFERENCE TO RELATED APPLICATION

This application is a Continuation of International Application No. PCT/ES01/00335, filed Sep. 4, 2001, the disclosure of which is incorporated herein by reference.

FIELD OF THE INVENTION

This invention relates to a process for obtaining 4-(N-alkylamino)-5,6-dihydro-4H-thien-(2,3-b)-thiopyran-2-sulfonamide-7,7-dioxides from the corresponding 4-(N-alkylamino)-5,6-dihydro-4H-thien-(2,3-b)-thiopyran-7,7-dioxides, which comprises protection of the alkylamino group, introduction of the sulfonamide group and the release of the protecting group. The invention also relates to the chiral starting materials for enantioselective synthesis of the compounds with optical isomerism and the synthesis intermediates formed while said process is being carried out.

BACKGROUND OF THE INVENTION

One of the current therapies for control of the elevated intraocular pressure, which seems to be related to the occurrence and progression of glaucoma, consists of the topical administration of carbonic anhydrase inhibitor. Spanish patent ES 2 053 738 describes, among others, some 4-(N-alkylamino)-5,6-dihydro-4H-thien-(2,3-b)-thiopyran-2-sulfonamide-7,7-dioxides of general formula (I):

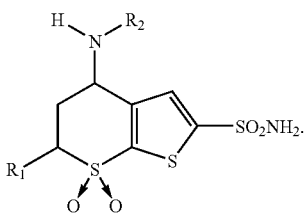

(I)

wherein $R_1$ is H or alkyl and $R_2$ is alkyl, which are active as inhibitors of carbonic anhydrase when administered topically. Of particular relevance is the compound (4S-trans)-4-(N-ethylamino)-5,6-dihydro-6-methyl-4H-thien-(2,3-b)-thiopyran-2-sulfonamide-7,7-dioxide, denominated dorzolamide, of formula Ia:

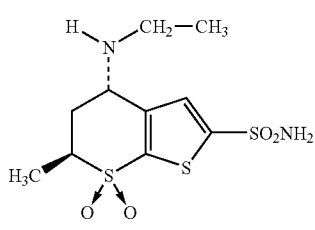

(Ia)

Said Spanish patent describes several processes for obtaining compounds of formula (I), which include the following:

1) oxidation of the corresponding 4-(N-alkylamino)-5,6-dihydro-4H-thien-(2,3-b)-thiopyran-2-sulfonamide with aqueous oxone in an organic solvent:

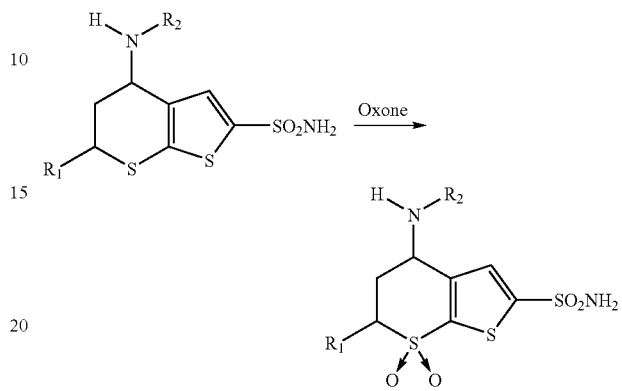

2) reduction of the corresponding derivative containing an N-acyl group:

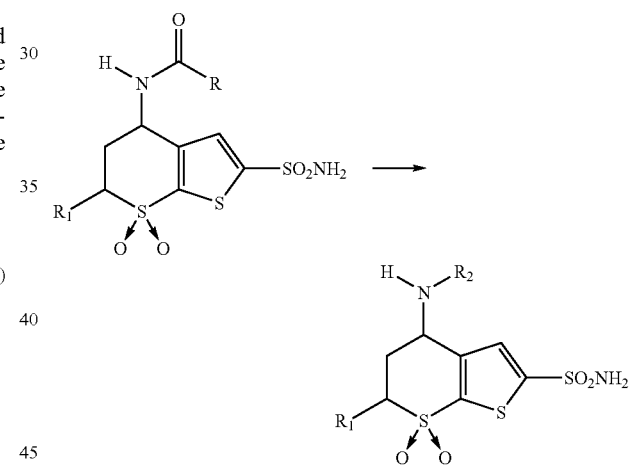

3) reacting the corresponding compound containing an hydroxy group in position 4 with toluenesulfonyl chloride followed by the addition of the desired alkylamine:

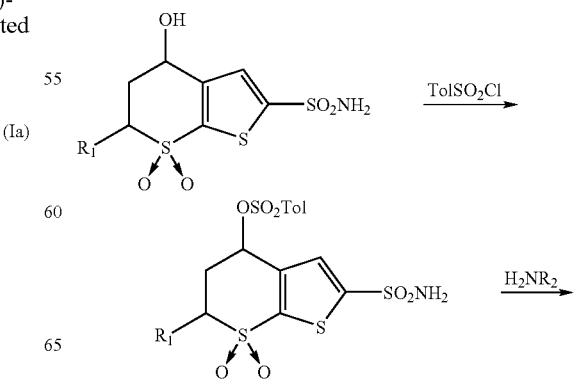

-continued

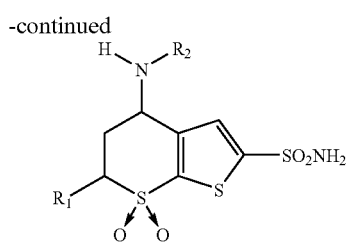

4) treating the corresponding compound containing a carbonyl group at position 4 with an amine in the presence of titanium tetrachloride, followed by reduction of the resulting intermediate with a metal hydride complex:

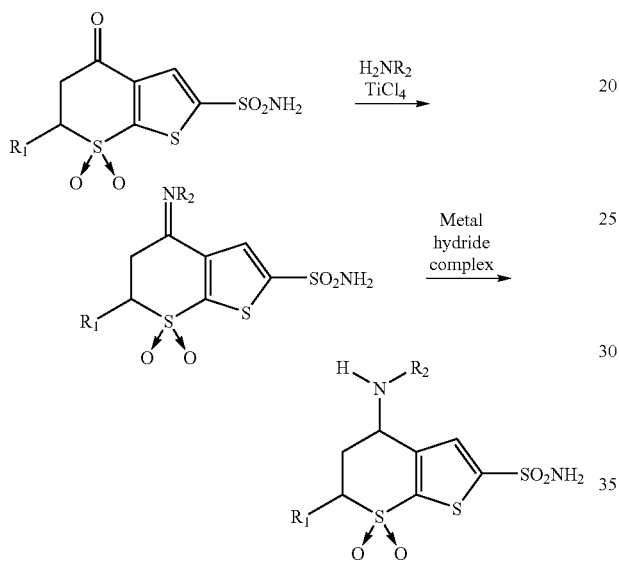

The aforementioned Spanish patent ES 2 053 738 describes the aforementioned processes for obtaining the cis or trans diasteroisomers, the levo or dextro enantiomers of said diastereomers or isomeric mixtures thereof.

The previously described processes have some drawbacks, which include:

when compound (I) is an enantiomer, for example, dorzolamide, the separation of the enantiomers is performed on the product of the last stage of synthesis, with the subsequent loss in the yield of the process because at least half of the material is lost when the entire synthesis has been performed;

in process 1) the last reaction is oxidation of the thioether group to a sulfone group, using oxone as an oxidant reagent; in these conditions, there is the risk of oxidation of the amine nitrogen, giving rise to by-groups that have to be removed during the purification of the final product;

process 2) comprises reduction of the amide group to amine as the last stage of the process, describing in said Spanish patent the use of diborane as a reducing agent, which has the drawback of having to perform the reaction under very energetic conditions in order to hydrolyse the borates which remain covalently bound to the product of the reaction; said reaction is performed by heating the reaction mixture under reflux with a mineral acid at a high concentration (for example, hydrochloric acid), which may give rise to the formation of by-products or alterations in the stereochemistry of the material with the subsequent potential problem of quality of the final product;

in process 3), the last reaction is a nucleophilic substitution reaction at the carbon in position 4; and, in the event that a specific geometric stereochemistry were required, as in the case of dorzolamide (trans), this reaction requires a complete inversion of the configuration because if not, it is necessary to separate the cis/trans mixtures formed, in addition to the separation of the enantiomers in the aforementioned final stage, with the subsequent loss of yield of the process; and in process 4), separation of the cis/trans diastereomers formed during reduction of the imino group is required.

Some of the problems mentioned above are solved in Spanish patent ES 2 112 482, where an enantioselective synthesis is described of compounds of formula (I), especially of dorzolamide, which uses the compound (4S-trans)-4-hydroxy- 5,6-dihydro-6-alkyl-4H-thien-(2,3-b)-thiopyran as starting material and follows the synthesis scheme shown below:

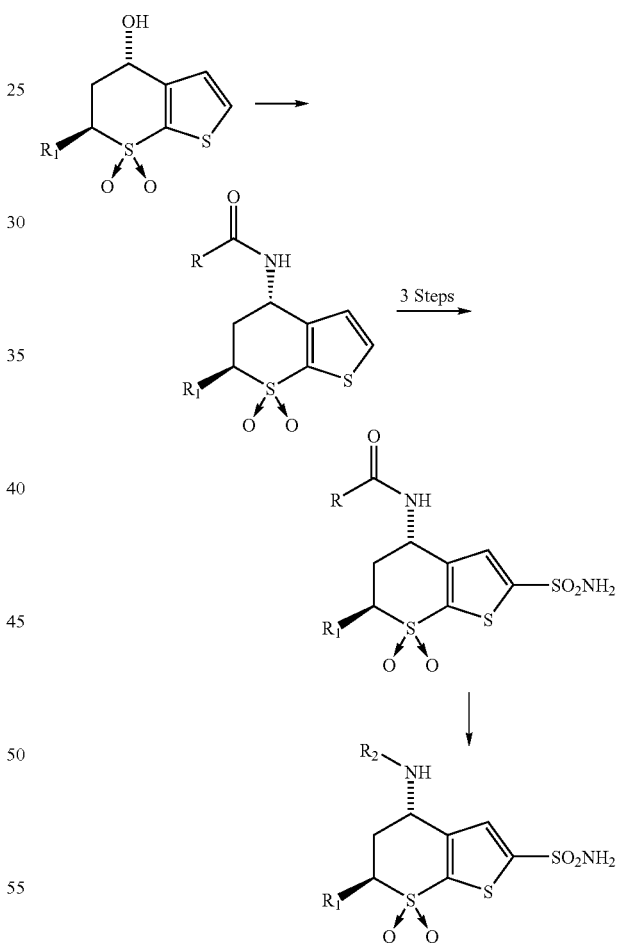

Chiral hydroxysulfone, the starting material of the synthesis, can be obtained by processes described in European Patents EP 658 211 and EP 590 549 or in U.S. Pat. Nos. 5,391,772, 5,474,919 and 5,760,249. In these processes, the chiral hydroxysulfone is obtained by asymmetric enzymatic reduction of the corresponding ketosulfone or by cyclation of the chiral thienyl thiobutyric acid, obtained in turn from a chiral hydroxyester or lactone, and subsequent stereospecific reduction of the ketone formed.

The key stage in this process is the conversion of the hydroxysulfone into the acetamidosulfone. This reaction is carried out by means of a Ritter Reaction which, in this case, takes place with retention of the configuration. The subsequent introduction of the sulfonamide group and the following reduction of the amide group to an amine lead to the desired product. Despite the fact that this process resolves some of the problems posed earlier regarding the processes described in patent ES 2 053 738, it has the drawbacks related with the fact that the last stage of the synthesis is reduction of the amide group to an amine with diborane. For this reason, the final purification process is complex and laborious.

SUMMARY OF THE INVENTION

The invention tackles the problem of providing an alternative process for the synthesis of 4-(N-alkylamino)-5,6-dihydro-4H-thien-(2,3-b)-thiopyran-2-sulfonamide-7,7-dioxides, which overcomes all or some of the aforementioned problems.

The solution presented by this invention consists in a process comprising the use of the corresponding 4-(N-alkylamino)-5,6-dihydro-4H-thien-(2,3-b)-thiopyran-7,7-dioxides as starting material and a synthesis strategy that comprises protection of the alkylamino group, the introduction of the sulfonamide group and the release of the protecting group. Operating in this fashion, said 4-(N-alkylamino)-5,6-dihydro-4H-thien-(2,3-b)-thiopyran-2-sulfonamide-7,7-dioxides are obtained in a simple and efficient way.

An advantage of the process provided by this invention lies in that a well-defined stereochemistry of the starting material can be used, as this configuration is not affected during the synthetic process (see, for example, Examples 3, 4, 6 and 8, related to synthesis of dorzolamide).

Therefore, an object of this invention consists of a process for obtaining 4-(N-alkylamino)-5,6-dihydro-4H-thien-(2,3-b)-thiopyran-2-sulfonamide-7,7-dioxides, from the corresponding 4-(N-alkylamino)-5,6-dihydro-4H-thien-(2,3-b)-thiopyran-2-sulfonamide-7,7-dioxides comprising the protection of the alkylamino group, the introduction of the sulfonamide group and the removal of the protecting group.

An additional object of this invention consists of a process for the enantioselective synthesis of an enantiomer of a 4-(N-alkylamino)-5,6-dihydro-4H-thien-(2,3-b)-thiopyran-2-sulfonamide-7,7-dioxide from the corresponding 4-(N-alkylamino)- 5,6-dihydro-4H-thien-(2,3-b)-thiopyran-7,7-dioxide with the appropriate stereochemistry, which comprises protection of the alkylamino group, introduction of the sulphonamide group and removal of the protecting group. Said chiral starting materials, in particular, the (4S-trans)-4-(N-alkylamino)-5,6-dihydro-6-alkyl-4H-thien-(2,3-b)-thiopyran-7,7-dioxides and the (4S)-4-(N-alkylamino)-5,6-dihydro-4H-thien-(2,3-b)-thiopyran-7,7-dioxides, constitute an additional object of this invention.

Another additional object of this invention consists of synthesis intermediates produced during the process provided by this invention.

DETAILED DESCRIPTION OF THE INVENTION

The invention provides a process for obtaining 4-(N-alkylamino)-5,6-dihydro-4H-thien-(2,3-b)-thiopyran-2-sulfonamide-7,7-dioxides of general formula (I)

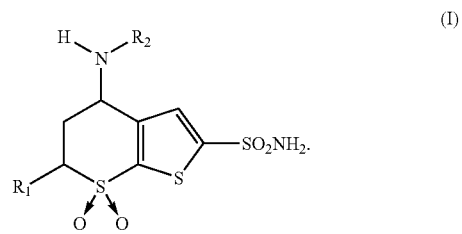

wherein
R$_1$ is H or C$_{1-5}$ alkyl, and
R$_2$ is C$_{1-5}$ alkyl, their individual cis or trans diastereomers, their individual levo or dextro enantiomers, or isomeric mixtures thereof, and pharmaceutically acceptable salts thereof, which comprises a) protecting the nitrogen present in the aminosulfone of formula (II)

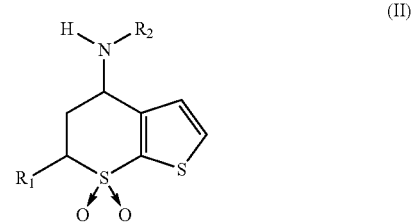

wherein R$_1$ and R$_2$ have been defined earlier, with a nitrogen protecting group to obtain an N-protected aminosulfone of formula (III)

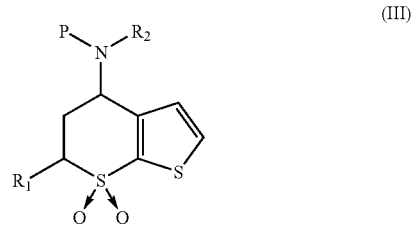

wherein R$_1$ and R$_2$ are as defined previously and P is a nitrogen protecting group;

b) introducing a sulfonamide group at position 2 of said N-protected aminosulfone (III) to obtain the sulfonamide intermediate of formula (VI)

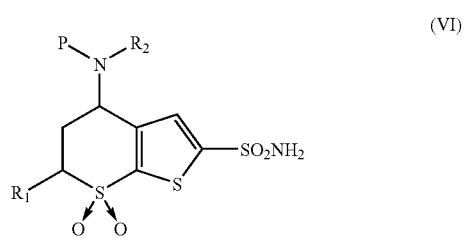

wherein $R_1$ and $R_2$ are as previously defined and P is a nitrogen protecting group; and c) eliminating the nitrogen protecting group to obtain the compound of formula (I).

In the sense using in this description, $C_{1-5}$ alkyl refers to a radical derived from an alkane, either linear or branched, of 1 to 5 carbon atoms, for example, methyl, ethyl or 2-methylpropyl.

A class of preferred compounds of general formula (I) is that in which the $R_1$ is $C_{1-5}$ alkyl, the stereochemical relation between the substituent groups of the carbons at positions 4 (C4) an 6 (C6) is trans and the chirality at C4 and C6 is S. A particularly preferred compound included within this class is dorzolamide [compound (I) in which $R_1$ is methyl, $R_2$ is ethyl, 4S, 6S, trans].

Another class of preferred compounds of general formula (I) is that in which $R_1$ is hydrogen and the chirality at C4 is S. A particularly preferred compound included within this class is sezolamide [4-(N-isobutylamino)-5,6-dihydro-4H-thien-(2,3-b)-thiopyran-2-sulfonamide-7,7-dioxide] [compound (I) in which $R_1$ is hydrogen, $R_2$ is isobutyl, 4S].

The process of the invention can be represented as shown in the following scheme.

gen, for example, acetamide, propionamide, benzamide, phenylacetamide or 2-chloroacetamide;

carbamates: P=$R_4$—O—CO—, where $R_4$ is alkyl, aryl or aralkyl, one or more hydrogens optionally substituted by halogen, for example, ethoxycarbonyl, phenoxycarbonyl, chloroethoxycarbonyl;

sulfonamides: P=$R_5$—$SO_2$—, where $R_5$ is alkyl or aryl, for example, methanosulfonamide or p-toluensulfonamide; and benzyl derivatives: P=Ar—$CH_2$—, where Ar represents optionally substituted phenyl, for example, benzyl or p-nitrobenzyl.

The racemic aminosulfone (II) [another way of naming the starting 4-(N-alkylamino)-5,6-dihydro-4H-thien-(2,3-b)-thiopyran-7,7-dioxide] is a known compound or can be obtained by conventional methods [see Examples 1 and 2].

The reaction for protecting the nitrogen present in the aminosulfone (II) is carried out under reaction conditions that depend on the selected protecting group. For example, for the formation of amides, aminosulfone (II) is reacted with an anhydride or corresponding acid chloride in an anhydrous solvent such as tetrahydrofuran (THF) or meth-

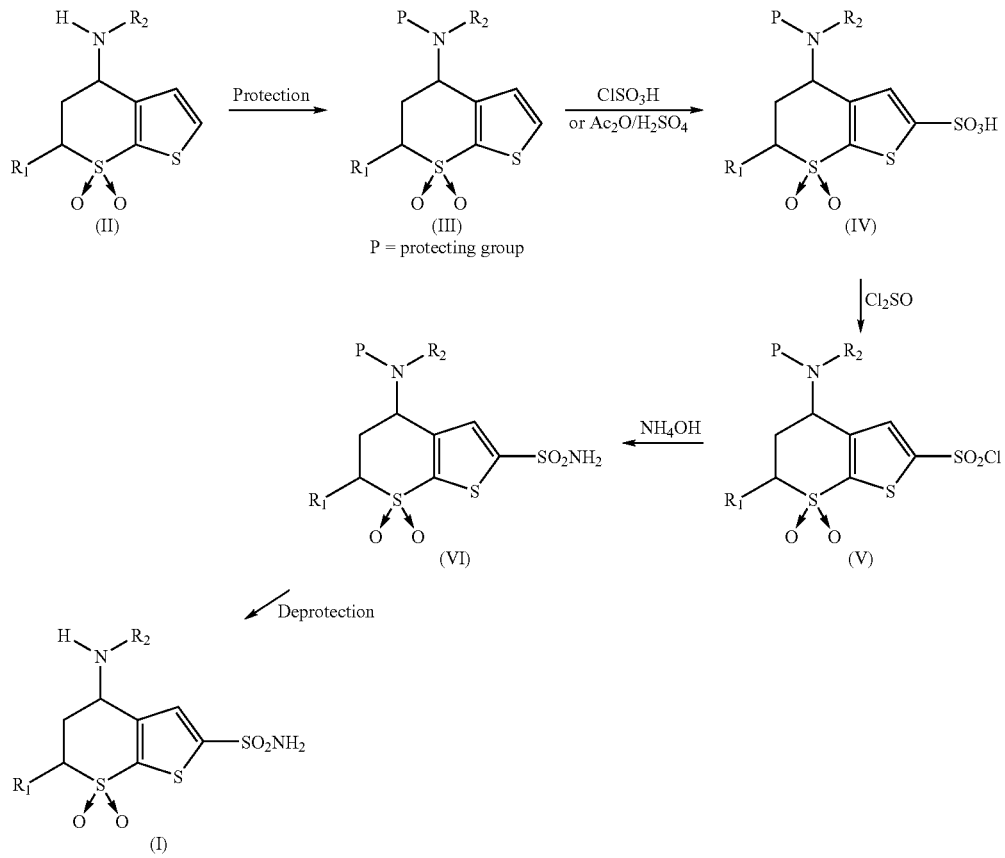

In accordance with the process of the invention, in the first stage [stage a)], the nitrogen group is protected in order to avoid sulfonylation thereof in the second stage [stage b)] of the process. Examples of protecting groups (P) of the nitrogen are as follows:

amides: P=$R_3$—CO—, where $R_3$ is alkyl, aryl or aralkyl, one or more hydrogens optionally substituted by haloylene chloride in the presence of an organic base. For the formation of carbamates, alkyl chloroformiate, aryl or aralkyl is reacted with aminosulfone (II) in an anhydrous aprotic solvent such as methylene chloride, in the presence of an organic base such as an amine. The formation of sulfonamides is carried out with sulfonyl chloride in the presence of pyridine or an aqueous base. The formation of the benzyl derivatives is carried out with a benzyl halide in a halogenated solvent in the presence of a base such as triethylamine.

In the case that compound (I) has geometric isomerism, for example, dorzolamide, the aminosulfone (II) has the geometric isomerism of compound (I). In a particular embodiment, aminosulfone (II) is a compound in which $R_1$ is $C_{1-5}$ alkyl, and the stereochemical relation between the substituent groups at C4 and C6 is trans.

In the case that compound (I) has optical isomerism, for example, dorzolamide or sezolamide, the chiral centres of the aminosulfone (II) may have the appropriate chirality, or, alternatively, a racemic mixture of (II) may be used. In the first case, the desired enantiomer of the aminosulfone (II) can be obtained from the racemic mixture by conventional techniques for resolving optical isomers, for example, by precipitation with an optically active acid (see Example 3) or by enzymatic resolution. In the case of using a racemic mixture of (II) as a starting material, the resulting compound (I) would have to be submitted to a final stage of resolution to obtain the desired enantiomer.

The introduction of the sulfonamide group to obtain the intermediate (VI) is carried out by means of a process that consists of the following three stages:
 i) the first stage consists of sulfonylation of the N-protected aminosulfone (III) by addition of chlorosulfonic acid or fuming sulphuric acid to it, at a temperature comprised between −10° C. and +5° C., followed by heating to a temperature comprised between 20° C. and 50° C., for a period of time comprised between 2 and 24 hours, to obtain the sulfonylated intermediate (IV) which does not need to be isolated and can be used directly in the following stage ii);
 ii) the second stage consists of a chloration of (IV), for which, over said intermediate (IV), thionyl chloride is added slowly at a temperature comprised between −5° C. and +30° C., followed by heating to a temperature comprised between 20° C. and 50° C., for a period of time comprised between 2 and 24 hours, to obtain the resulting intermediate (V), which is isolated, for example, by addition of the reaction mixture to a mixture of water/ice in which intermediate (V) precipitates, and is filtered; and
 iii) the third stage consists of the formation of the sulphonamide (VI) for which the intermediate (V) is added to a mixture of THF/aqueous ammonia, at a temperature comprised between −5° C. and +10° C., followed by neutralisation of the reaction mixture, elimination of the organic solvent and isolation of (VI) by conventional method, for example, by filtration.

The last stage of the process of the invention [stage c)] comprises the elimination of the nitrogen protecting group to obtain (I). This reaction depends on the protecting group present in (VI). For the amide, carbamate or sulfonamide protecting groups, this reaction is carried out in mineral acid medium, for example, hydrochloric acid, sulphuric acid, hydrobromic acid or perchloric acid, in water or in a protic organic solvent, such as acetic acid, and at temperatures comprised between room temperature (15° C.–25° C.) and the reflux temperature of the medium. The product, as a free base, is isolated by neutralisation of the acid and extraction into an organic solvent, for example, ethyl acetate. In the case of protection with a benzyl group, this can be eliminated by catalytic hydrogenation using a catalyst such as Raney Nickel, Pd on carbon, etc.

An additional feature of the process of the invention, and one which supposes an advantage thereof, is that a starting material with a defined stereochemistry (II) can be used, given that it has been observed that said configuration is not altered during the synthetic process. Thus, for example, if a racemic mixture of trans-4-(N-alkylamino)-5,6-dihydro-6-alkyl-4H-thien-(2,3-b)-thiopyran-7,7-dioxide (compound (II) racemic trans, $R_1$=$C_{1-5}$ alkyl) is used as starting material, the racemic mixture of trans-4-(N-alkylamino)-5,6-dihydro-6-alkyl-4H-thien-(2,3-b)-thiopyran-2-sulfonamide-7,7-dioxide (compound (I) racemic trans; R=$C_{1-5}$ alkyl) is obtained without obtaining appreciable quantities of the cis isomer. In the event that the starting material is (4S-trans)-4-(N-alkylamino)-5,6-dihydro-6-alkyl-4H-thien-(2,3-b)-thiopyran-7,7-dioxide (compound (II) trans enantiomers S,S, $R_1$=$C_{1-5}$ alkyl) or else (4S)-4-(N-alkylamino)-5,6-dihydro-4H-thien-(2,3-b)-thiopyran-7,7-dioxide (compound (II) enantiomer S, $R_1$=H), (4S-trans)-4-(N-alkylamino)-5,6-dihydro-6-alkyl-4H-thien-(2,3-b)-thiopyran-2-sulfonamide-7,7-dioxide (compound (I) trans enantiomer S,S, $R_1$=$C_{1-5}$ alkyl) or (4S)-4-(N-alkylamino)-5,6-dihydro-4H-thien-(2,3-b)-thiopyran-2-sulfonamide-7,7-dioxide (compound (I) enantiomer S, $R_1$=H) is obtained, respectively, without obtaining appreciable quantities of the cis isomer or observing racemisation of the centre or the chiral centres.

Said chiral starting materials, specifically, the enantiomers:
 i) (4S-trans)-4-(N-alkylamino)-5,6-dihydro-6-alkyl-4H-thien-(2,3-b)-thiopyran-7,7-dioxide (IIa)

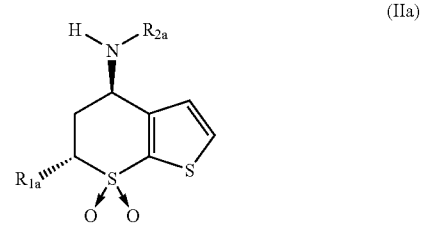

(IIa)

wherein
 $R_{1a}$ and $R_{2a}$, independently, are $C_{1-5}$ alkyl, and
 ii) (4S)-(N-alkylamino)-5,6-dihydro-4H-thien-(2,3-b)-thiopyran-7,7-dioxide (IIb)

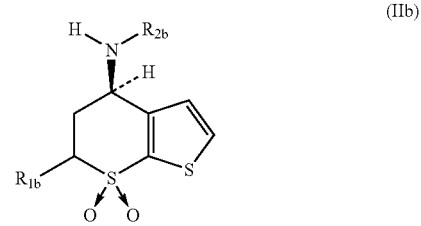

(IIb)

wherein
 $R_{1b}$ is H, and
 $R_{2b}$ is $C_{1-5}$ alkyl,
form part of the present invention and constitute an additional object thereof. Said enantiomers can be obtained from their racemic mixtures by conventional optical isomers resolution methods, for example, by precipitation with an optically active acid or by enzymatic resolution. Illustrative examples of said chiral starting materials (IIa) and (IIb) include (4S-trans)-4-(N-ethylamino)-5,6-dihydro-6-methyl- 4H-thien-(2,3-b)-thiopyran-7,7-dioxide and (4S)-4-(N-isobutylamino)-5,6-dihydro-4H-thien-(2,3-b)-thiopyran-7,7-dioxide.

Therefore, in a further aspect, the invention provides a process for the enantioselective synthesis of an enantiomer of 4-(N-alkylamino)-5,6-dihydro-4H-thien-(2,3-b)-thiopyran-2-sulfonamide-7,7-dioxide (I), from the corresponding 4-(N-alkylamino)-5,6-dihydro-4H-thien-(2,3-b)-thiopyran-7,7-dioxide with the appropriate stereochemistry, comprising the protection of the alkylamino group, the introduction of the sulfonamide group and the removal of the protecting group.

In a particular embodiment, the invention provides a process for the enantioselective synthesis of a (4S)-4-(N-alkylamino)-5,6-dihydro-4H-thien-(2,3-b)-thiopyran-2-sulphonamide-7,7-dioxide [compound (I), 4S enantiomer], from the corresponding (4S)-4-(N-alkylamino)-5,6-dihydro-4H-thien-(2,3-b)-thiopyran-2-dioxide [compound (IIb)] which comprises the protection of the alkylamino group, the introduction of the sulfonamide group and the release of the protecting group by stages a), b) and c), mentioned previously in relation to the general process of the invention. A specific application of this alternative leads to the enantioselective synthesis of sezolamide from the corresponding chiral intermediates.

In another particular embodiment, the invention provides a process for the enantioselective synthesis of (4S-trans)-4-(N-alkylamino)-5,6-dihydro-6-alkyl-4H-thien-(2,3-b)-thiopyran-2-sulfonamide-7,7-dioxide [compound (I) in which $R_1$ is $C_{1-5}$ alkyl, the geometric isomery is trans, and the chirality is 4S and 6S], from the corresponding (4S-trans)-4-(N-alkylamino)-5,6-dihydro-6-alkyl-4H-thien-(2,3-b)-thiopyran-7,7-dioxide [compound (IIa)], which comprises protecting the alkylamino group, the introduction of the sulfonamide group and the removal of the protecting group by means of stages a), b) and c) previously mentioned in relation to the general process of the invention. A specific application of this alternative leads to the enantioselective synthesis of dorzolamide from the corresponding diastereomeric and chiral intermediates.

The intermediates of general formula (III), (IV), (V) and (VI), their individual cis and trans diastereomers, its individual levo or dextro enantiomers, or isomeric mixtures thereof, form part of the invention and constitute an additional object thereof. Illustrative examples of said intermediates include the following compounds:

Intermediates of Formula (III):
4-(N-acetyl-N-ethylamino)-5,6-dihydro-6-methyl-4H-thien-(2,3-b)-thiopyran-7,7-dioxide, its individual cis or trans diastereomers, its individual levo or dextro enantiomers, or isomeric mixtures thereof; and 4-(N-acetyl-N-isobutylamino)-5,6-dihydro-4H-thien-(2,3-b)-thiopyran-7,7-dioxide, its individual cis or trans diastereomers, its individual levo or dextro enantiomers, or isomeric mixtures thereof.

Intermediates of Formula (IV)
4-(N-acetyl-N-ethylamino)-5,6-dihydro-6-methyl-4H-thien-(2,3-b)-thiopyran-7,7-dioxide 2-sulfonic acid, its individual cis or trans diastereomers, its individual levo or dextro enantiomers, or isomeric mixtures thereof; and 4-(N-acetyl-N-isobutylamino)-5,6-dihydro-4H-thien-(2,3-b)-thiopyran-7,7-dioxide 2-sulfonic acid, its individual cis or trans diastereomers, its individual levo or dextro enantiomers, or isomeric mixtures thereof.

Intermediates of Formula (V)
4-(N-acetyl-N-ethylamino)-5,6-dihydro-6-methyl-4H-thien-(2,3-b)-thiopyran-7,7-dioxide 2-sulfonic acid chloride, its individual cis or trans diastereomers, its individual levo or dextro enantiomers, or isomeric mixtures thereof; and 4-(N-acetyl-N-isobutylamino)-5,6-dihydro-4H-thien-(2,3-b)-thiopyran-7,7-dioxide 2-sulfonic acid chloride, its individual cis or trans diastereomers, its individual levo or dextro enantiomers, or isomeric mixtures thereof; and Intermediates of Formula (VI)
4-(N-acetyl-N-ethylamino)-5,6-dihydro-6-methyl-4H-thien-(2,3-b)-thiopyran-7,7-dioxide 2-sulfonamide, its individual cis or trans diastereomers, its individual levo or dextro enantiomers, or isomeric mixtures thereof; and 4-(N-acetyl-N-isobutylamino)-5,6-dihydro-4H-thien-(2,3-b)-thiopyran-7,7-dioxide 2-sulfonamide, its individual cis or trans diastereomers, its individual levo or dextro enantiomers, or isomeric mixtures thereof.

The following examples illustrate the invention and should not be considered as limiting the scope thereof.

EXAMPLE 1

Trans-4-(N-ethylamino)-5,6-dihydro-6-methyl-4H-thien-(2,3-b)-thiopyran-7,7-dioxide

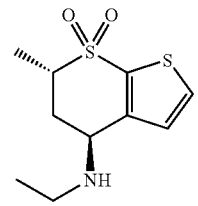

26 ml (0.2 mol) of 2 M boroetherate trifluoride in a solution of tetrahydrofuran are added to a solution of 4-(N-acetamido)-5,6-dihydro-6-methyl-4H-thien-(2,3-b)-thiopyran-7,7-dioxide (26 g, 0.1 mol) in tetrahydrofuran (320 ml), cooled to between 0 and 5° C. After the addition, the mixture is shaken at room temperature, and sodium borohydride (7.7 g, 0.2 mol) is added. The mixture is kept at room temperature for 1 hour and then poured onto a solution of 4 N hydrochloric acid. It is stirred at room temperature for 1 hour and then the pH is set to 8 with sodium hydroxide. The crude product is extracted three times with ethyl acetate, and the organic extracts are pooled, dried and concentrated to dryness. The crude product is submitted to silica gel chromatography using a mixture THF/Et$_3$N (50/3) as solvent, yielding 12 g (49%) of the title product.

$^1$H NMR (CDCl$_3$, 300 MHz): δ 1.08 (t, 3H), 1.43 (d, 3H), 2.29 (m, 2H), 2.72 (m, 2H), 3.77 (m, 1H), 3.89 (m, 1H), 6.98 (d, 1H), 7.51 (d, 1H); $^{13}$C NMR (CDCl$_3$, 300 MHz): 10.7, 15.2, 34.9, 41.9, 51.0, 52.1, 127.1, 130.5, 135.3, 145.4.

EXAMPLE 2

4-(N-isobutylamino)-5,6-dihydro-4H-thien-(2,3-b)-thiopyran-7,7-dioxide

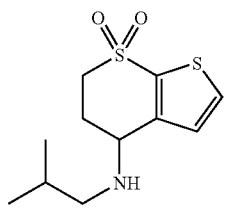

15 ml (0.036 mol) of diborane dimethylsulphide complex in a solution of 2M tetrahydrofuran are added to a solution of 4-(N-isobutyrylamino)-5,6-dihydro-4H-thien-(2,3-b)-thiopyran-7,7-dioxide (5 g, 0.18 mol) in tetrahydrofuran (30 ml), cooled to between 0 and 5° C. After the addition, the mixture is stirred at room temperature for 2 hours. The crude product is neutralised with water and concentrated under vacuum to a thick oil. A solution of 4N hydrochloric acid is added and the mixture kept at room temperature for 1 hour. The pH is set to 8 with sodium hydroxide and the crude extracted three times with ethyl acetate, and the organic extracts are pooled, dried and concentrated to dryness. The crude product is submitted to silica gel chromatography using a mixture $CH_2Cl_2$/MeOH (94/6) as solvent, yielding 2.3 g (49%) of the title product.

$^1$H NMR (CDCl$_3$, 300 MHz): δ 7.46 (d, 1H), 6.92 (d, 1H), 6.84 (d, 1H), 5.18 (m, 1H), 3.34 (m, 2H), 2.51 (m, 1H), 2.43 (m, 2H), 1.11 (d, 6H); $^{13}$C NMR (CDCl$_3$, 300 MHz): 146.0, 135.4, 130.1, 129.0, 127.0, 54.4, 52.1, 49.2, 28.4, 27.3, 20.3, 20.2.

EXAMPLE 3

(4S-trans)-4-(N-ethylamino)-5,6-dihydro-6-methyl-4H-thien-(2,3-b)-thiopyran-7,7-dioxide Stage A: Preparation of the (−)-Tartaric Salt A racemic mixture of trans-4-(N-ethylamino)-5,6-dihydro-6-methyl-4H-thien-(2,3-b)-thiopyran-7,7-dioxide (5 g, 0.022 mol) in isopropanol/water (100/2) (100 ml) is heated until it dissolves. While hot, (−)-di-p-tolyl-tartaric acid (3.6 g, 0.01 mol) is added and the mixture allowed to cool slowly. When it has reached room temperature, the resulting solid is filtered to give 4.6 g of salt.

The solid is suspended once more in 96 ml of the mixture of water and alcohol, and heated under reflux and cooled to room temperature to yield 3.3 g of product. The operation is repeated for a third time, yielding 2.9 g of tartaric salt.

Stage B: Release of the Amine

The tartaric salt obtained in Stage A is suspended in water and the pH adjusted to 8. The mixture is extracted 3 times with ethyl acetate, and the organic extracts are pooled, dried and concentrated to dryness, obtaining 0.75 g (15%) of title product with a rotary power of $[α]_D$=−90° (c=1, methanol).

$^1$H NMR (CDCl$_3$, 300 MHz): δ 1.08 (t, 3H), 1.43 (d, 3H), 2.29 (m, 2H), 2.72 (m, 2H), 3.77 (m, 1H), 3.89 (m, 1H), 6.98 (d, 1H), 7.51 (d, 1H); $^{13}$C NMR (CDCl$_3$, 300 MHz): 10.7, 15.2, 34.9, 41.9, 51.0, 52.1, 127.1, 130.5, 135.3, 145.4.

EXAMPLE 4

Obtaining N-Protected Aminosulfones (III)

Example 4a (4S-trans)-4-(N-acetyl-N-ethylamino)-5,6-dihydro-6-methyl-4H-thien-(2,3-b)-thiopyran-7,7-dioxide

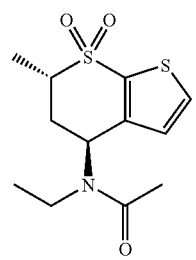

A solution of α-chloroacetyl chloride (3.68 ml, 0.052 mol) in tetrahydrofuran is added dropwise to a solution of (4S-trans)-4-(N-ethylamino)-5,6-dihydro-6-methyl-4H-thien-(2,3-b)-thiopyran-7,7-dioxide (12 g, 0.048 mol) and triethylamine (14.8 ml, 1.06 mol) under a nitrogen atmosphere. Once the addition is complete, the mixture is kept at room temperature for 15 minutes and a saturated solution of bicarbonate is added until the medium is neutralised. It is extracted 3 times with ethyl acetate. The extracts are dried and concentrated to dryness to give 12 g (88%) of the title product, with a rotary power of $[α]_D$=−100° (c=1, methanol).

$^1$H NMR (CDCl$_3$, 300 MHz): δ 1.15 (t, 3H), 1.52 (d, 3H), 2.1 (s, 3H), 2.43 (m, 1H), 2.82 (m, 1H), 3.15 (m, 1H), 3.31 (m, 1H), 3.60 (m, 1H), 5.95 (m, 1H), 6.81 (d, 1H), 7.60 (d, 1H); $^{13}$C NMR (CDCl$_3$, 300 MHz): 12.1, 15.9, 21.5, 32.6, 40.3, 46.9, 55.9, 126.6, 130.4, 134.8, 142.5, 175.1.

Example 4b

Trans-4-(N-propanoyl-N-ethylamino)-5,6-dihydro-6-methyl-4H-thien-(2,3-b)-thiopyran-7,7'-dioxide

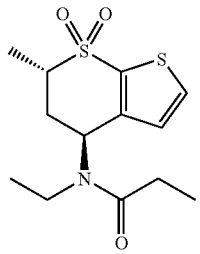

This is prepared according to the process described in Example 4a, from 2 g (0.008 mol) of trans-4-(N-ethylamino)-5,6-dihydro-6-methyl-4H-thien-(2,3-b)-thiopyran-7,7-dioxide, 25 ml of methylene chloride, 1.4 ml (0.010 mol) of triethylamine and 1.28 ml (0.010 mol) of propionic anhydride. 2.1 g (87%) of the title product are obtained.

$^1$H NMR (CDCl$_3$, 300 MHz): δ 1.10 (m, 6H), 1.45 (m, 2H), 2.40 (m, 3H), 2.75 (m, 1H), 3.05 (m, 1H), 3.20 (m, 1H), 3.55 (m, 1H), 5.95 (m, 1H), 6.75 (d, 1H), 7.60 (d, 1H).

Example 4c

Trans-4-(N-(2-chloroacetyl)-N-ethylamino)-5,6-dihydro-6-methyl-4H-thien-(2,3-b)-thiopyran-7,7-dioxide

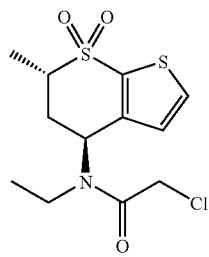

This is prepared according to the process described in Example 4a, from 2 g (0.008 mol) of trans-4-(N-ethylamino)-5,6-dihydro-6-methyl-4H-thien-(2,3-b)-thiopyran-7,7-dioxide, 25 ml of methylene chloride, 0.66 ml (0.008 moles) of pyridine and 0.65 ml (0.008 moles) of α-chloroacetyl chloride. 1.6 g (62%) of the title product are obtained.

$^1$H NMR (CDCl$_3$, 300 MHz): δ 1.20 (t, 3H), 1.55 (m, 3H), 2.48 (m, 1H), 2.90 (m, 1H), 3.25 (m, 1H), 3.40 (m, 1H), 3.60 (m, 1H), 4.22 (s, 2H), 5.85 (m, 1H), 6.85 (d, 1H), 7.65 (d, 1H).

Example 4d

Trans-4-(N-benzoyl-N-ethylamino)-5,6-dihydro-6-methyl-4H-thien-(2,3-b)-thiopyran-7,7-dioxide

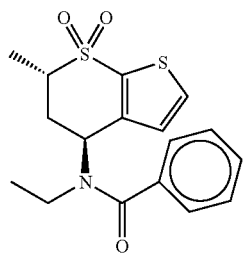

This is prepared according to the process described in Example 4a, from 2 g (0.008 mol) of trans-4-(N-ethylamino)-5,6-dihydro-6-methyl-4H-thien-(2,3-b)-thiopyran-7,7-dioxide, 25 ml of methylene chloride, 0.66 ml (0.008 moles) of pyridine and 0.95 ml (0.008 mol) of acetyl chloride. An oil purified by silica gel chromatography is obtained using a mixture of heptane/ethyl acetate (10/20), 1.8 g (67%) of the title product are obtained.

$^1$H NMR (CDCl$_3$, 300 MHz): δ 1.20 (t, 3H), 1.52 (m, 3H), 2.43 (m, 1H), 2.82 (m, 1H), 3.15 (m, 1H), 3.28 (m, 1H), 3.55 (m, 1H), 5.85 (m, 1H), 6.81 (d, 1H), 7.45 (m, 5H), 7.60 (d, 1H).

EXAMPLE 5

4-(N-acetyl-N-isobutylamino)-5,6-dihydro-4H-thien-(2,3-b)-thiopyran-7,7-dioxide

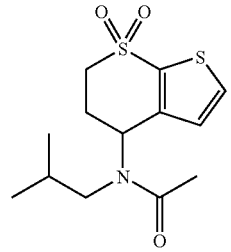

This is prepared following the process of Example 4a, from 4 g (0.015 mol) of 4-(N-isobutylamino)-5,6-dihydro-4H-thien-(2,3-b)-thiopyran-7,7-dioxide, 5.1 ml (0.037 mol) of triethylamine and 1.4 ml (0.02 mol) of α-chloroacetyl chloride. 3.8 g (80%) of the title product is obtained.

$^1$H NMR (CDCl$_3$, 300 MHz): δ 7.53 (d, 1H), 6.75 (d, 1H), 5.48 (m, 1H), 3.53 (m, 2H), 3.34 (m, 1H), 2.52 (m, 1H), 2.17 (s, 3H), 1.85 (m, 1H), 1.11 (d, 6H); $^{13}$C NMR (CDCl$_3$, 300 MHz): 171.6, 143.5, 135.5, 130.8, 126.2, 51.9, 28.3, 26.7, 22.4, 20.1.

EXAMPLE 6

Obtaining N-Protected Sulfonamidated Intermediates (VI)

Example 6a (4S-trans)-4-(N-acetyl-N-ethylamino)-5,6-dihydro-6-methyl-4H-thien-(2,3-b)-thiopyran-2-sulfonamide-7,7-dioxide

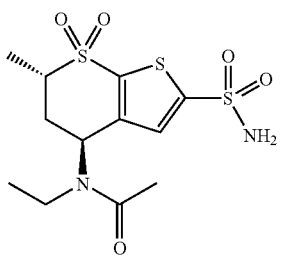

Stage A: Preparation of the Acid Chloride 4 g (0.013 mol) of (4S-trans)-4-(N-acetyl-N-ethylamino)-5,6-dihydro-6-methyl-4H-thien-(2,3-b)-thiopyran-7,7-dioxide are added to 7.4 ml (0.11 mol) of chlorosulfonic acid cooled to 0° C. Once the addition has finished, the mixture is heated to 50° C. for 12 h, then cooled once again to 0° C. Thionyl chloride (7.42 ml, 0.1 mol) is added slowly dropwise to the solution. The mixture is heated once again to 50° C. for 12 hours. The crude product is cooled to room temperature and poured over a water/ice mixture, obtaining a pinkish solid, which is filtered and immediately incorporated into the following stage of the synthesis.

Stage B: Obtaining Sulfonamide

The solid obtained from Stage A is added slowly to a mixture of tetrahydrofuran (25 ml) and 15% ammonia (5 ml), cooled to 0° C. Once the addition is over, stirring is maintained until dissolution is complete. The crude product is concentrated to dryness and submitted to silica gel chromatography using a mixture of CH$_2$Cl$_2$/MeOH (50/3.5) as solvent, obtaining 2.3 g (47%) of the title product, with a rotary power of [α]$_D$=−80° (c=1, methanol).

$^1$H NMR (DMSO-d$_6$, 300 MHz): δ 1.14 (t, 3H), 1.41 (d, 3H), 2.05 (s, 3H), 2.43 (m, 1H), 2.78 (m, 1H), 3.26 (m, 1H), 3.46 (m, 1H), 3.55 (m, 1H), 3.91 (m, 1H), 4.40 (m, 1H), 5.21 (1H, m), 7.24 (s, 1H), 8.02 (s, 2H); $^{13}$C NMR (DMSO-d$_6$, 300 MHz) 11.6, 15.2, 21.9, 32.4, 42.7, 55.4, 62.2, 128.4, 136.2, 144.6, 149.4, 170.3.

Example 6b

Trans-4-(N-propanoyl-N-ethylamino)-5,6-dihydro-6-methyl-4H-thien-(2,3-b)-thiopyran-2-sulfonamide-7,7-dioxide

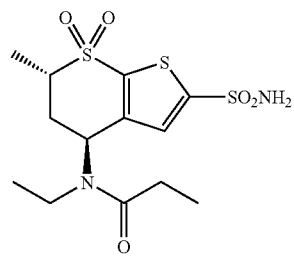

Stage A: Preparation of the Acid Chloride

This is prepared following the process of Example 6a (Stage A), from 2.15 g (0.0075 mol) of trans-4-(N-propanoyl-N-ethylamino)-5,6-dihydro-6-methyl-4H-thien-(2,3-b)-thiopyran-7,7-dioxide, 4.1 ml (0.06 mol) of chlorosulfonic acid and 4.1 ml (0.055 mol) of thionyl chloride, yielding a pink coloured solid that is immediately incorporated in the following step of the reaction.

Stage B: Obtaining Sulfonamide

This is obtained following the process of Example 6a (Stage B), from acid chloride isolated from the previous step, 15 ml of tetrahydrofuran and 5 ml of 20% ammonia. 2.2 g of crude product are obtained that are submitted to silica gel chromatography using a CH$_2$Cl$_2$/MeOH (50/3) mixture as a solvent, obtaining 1.9 g (69%) of the title product.

$^1$H NMR (DMSO-d$_6$, 300 MHz): δ 1.05 (t, 3H), 1.18 (t, 3H), 1.45 (d, 3H), 2.43 (m, 3H), 2.75 (m, 2H), 3.26 (m, 1H), 3.45 (m, 1H), 3.95 (m, 1H), 5.21 (1H, m), 7.20 (s, 1H), 8.05 (s, 2H).

Example 6c

Trans-4-(N-(2-chloroacetyl)-N-ethylamino)-5,6-dihydro-6-methyl-4H-thien-(2,3-b)-thiopyran-2-sulfonamide-7,7-dioxide

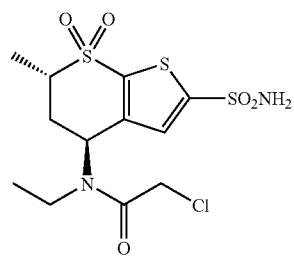

Stage A: Preparation of the Acid Chloride

This is prepared following the process of Example 6a (Stage A), from 1.6 g (0.0053 mol) of trans-4-(N-(2-chloroacetyl)-N-ethylamino)-5,6-dihydro-6-methyl-4H-thien-(2,3-b)-thiopyran-7,7-dioxide, 3 ml (0.044 mol) of chlorosulphonic acid and 3 ml (0.040 mol) of thionyl chloride, yielding a pink coloured solid that is immediately incorporated in the following step of the reaction.

Stage B: Obtaining Sulfonamide

This is obtained following the process of Example 6a (Stage B), from acid chloride isolated from the previous step, 7.5 ml of tetrahydrofuran and 4 ml of 20% ammonia. 2.2 g of crude product is obtained that is submitted to silica gel chromatography using a mixture of CH$_2$Cl$_2$/MeOH (95/5) as a solvent, obtaining 1.18 g (58%) of the title product.

Example 6d

Trans-4-(N-benzoyl-N-ethylamino)-5,6-dihydro-6-methyl-4H-thien-(2,3-b)-thiopyran-2-sulfonamide-7,7-dioxide

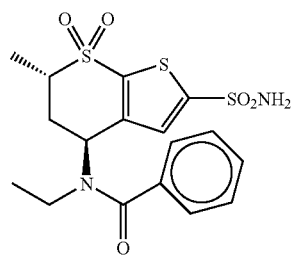

Stage A: Preparation of the Acid Chloride

This is prepared following the process of Example 6a (Stage A), from 1.2 g (0.0035 mol) of trans-4-(N-benzoyl-N-ethylamino)-5,6-dihydro-6-methyl-4H-thien-(2,3-b)-thiopyran-7,7-dioxide, 3 ml (0.044 mol) of chlorosulphonic acid and 3 ml (0.040 mol) of thionyl chloride, yielding a pink coloured solid that is immediately incorporated in the following step of the reaction.

Stage B: Obtaining Sulfonamide

This is obtained following the process of Example 6a (Stage B), from acid chloride isolated from the previous step, 7.5 ml of tetrahydrofuran and 4 ml of 20% ammonia. 2.2 g of crude product is obtained that is submitted to silica gel chromatography using a mixture of CH$_2$Cl$_2$/MeOH (50/2) as a solvent, obtaining 1.05 g (72%) of the title product.

EXAMPLE 7 b 4-(N-acetyl-N-isobutylamino)-5,6-dihydro-4H-thien-(2,3-b)-thiopyran-2-sulfonamide-7,7-dioxide

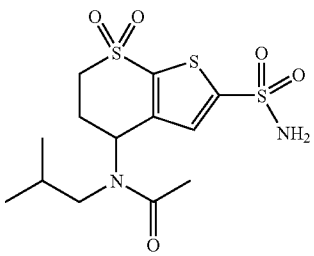

Stage A: Preparation of the Acid Chloride

This is prepared following the process of Example 6a (Stage A), from 2 g (0.0064 mol) of 4-(N-acetyl-N-isobutylamino)-5,6-dihydro-4H-thien-(2,3-b)-thiopyran-7,7-dioxide, 4.1 ml (0.06 mol) of chlorosulphonic acid and 4.1 ml (0.055 mol) of thionyl chloride, yielding a light pink coloured solid that is immediately incorporated in the following step of the reaction.

Stage B: Obtaining Sulfonamide

This is obtained following the process of Example 6a (Stage B), from acid chloride isolated in Stage A, 15 ml of tetrahydrofuran and 5 ml of 20% ammonia. 2.2 g of crude product are obtained that are submitted to silica gel chromatography using a $CH_2Cl_2/MeOH$ (47/3) mixture as a solvent, obtaining 1.35 g (54%) of the title product.

$^1$H NMR (CDCl$_3$, 300 MHz): δ 8.05 (s, 2H), 7.20 (s, 1H), 4.76 (m, 1H), 3.72 (m, 2H), 3.23 (m, 2H), 2.95 (m, 1H), 2.30 (m, 1H), 2.03 (s, 3H), 1.83 (m, 1H), 1.00 (d, 6H); $^{13}$C NMR (CDCl$_3$, 300 MHz): 170.3, 148.6, 145.7, 136.3, 127.7, 62.0, 27.6, 25.8, 25.5, 22.5, 20.0, 19.5.

EXAMPLE 8

Obtaining Compounds (I) in Which $R_1$ is Methyl

Example 8a (4S-trans)-4-(N-ethylamino)-5,6-dihydro-6-methyl-4H-thien-(2,3-b)-thiopyran-2-sulfonamide-7,7-dioxide

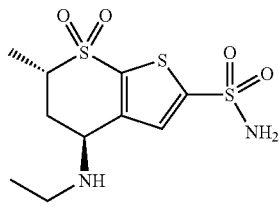

1 g (0.0027 mol) of (4S-trans)-4-(N-acetyl-N-ethylamino)-5,6-dihydro-6-methyl-4H-thien-(2,3-b)-thiopyran-2-sulfonamide-7,7-dioxide is dissolved in 16 ml of a mixture of methanol/hydrochloric acid 36% (1/1). The solution is heated under reflux for 72 h. It is cooled to room temperature and poured over water and neutralised with a solution of saturated bicarbonate. It is extracted 3 times with ethyl acetate, and the organic phases are pooled, dried and concentrated to dryness. The residue is submitted to silica gel chromatography using the a mixture of THF/Et$_3$N (50/2) as a solvent, obtaining 0.55 g (66%) of the title product, with a rotary power of $[α]_D=-32°$ (c=1, methanol).

$^1$H NMR (DMSO-d$_6$, 300 MHz): δ 1.28 (t, 3H), 1.37 (d, 3H), 2.53 (m, 1H), 2.80 (m, 1H), 3.04 (m, 1H), 3.19 (m, 1H), 4.36 (m, 1H), 4.69 (1H, m), 8.01 (s, 1H), 8.21 (s, 2H), 9.60 (m, 1H); 9.89 (m, 1H); $^{13}$C NMR (DMSO-d$_6$, 300 MHz): 9.9, 11.1, 30.6, 40.7, 49.1, 51.5, 54.5, 130.7, 137.3, 141.8, 149.6.

Example 8b

Trans-4-(N-ethylamino)-5,6-dihydro-6-methyl-4H-thien-(2,3-b)-thiopyran-2-sulfonamide-7,7-dioxide This is prepared following the process of Example 8a, from 0.25 g (0.0015 mol) of 4-(N-propionyl-N-isobutylamino)-5,6-dihydro-4H-thien-(2,3-b)-thiopyran-7,7-dioxide. The crude product is submitted to silica gel chromatography using a mixture of THF/Et$_3$N (50/2) as solvent, obtaining 0.09 g (40%) of the title product.

Example 8c

Trans-4-(N-ethylamino)-5,6-dihydro-6-methyl-4H-thien-(2,3-b)-thiopyran-2-sulfonamide-7,7-dioxide This is prepared following the process of Example 8a, from 0.25 g (0.0006 mol) of 4-(N-(2-chloroacetyl)-N-isobutylamino)-5,6-dihydro-4H-thien-(2,3-b)-thiopyran-7,7-dioxide. The crude product is submitted to silica gel chromatography using a mixture of THF/Et$_3$N (50/2) as solvent, obtaining 0.08 g (38%) of the title product.

Example 8d

Trans-4-(N-ethylamino)-5,6-dihydro-6-methyl-4H-thien-(2,3-b)-thiopyran-2-sulfonamide-7,7-dioxide This is prepared following the process of Example 8a, from 0.25 g (0.0006 mol) of 4-(N-benzoyl-N-isobutylamino)-5,6-dihydro-4H-thien-(2,3-b)-thiopyran-7,7-dioxide. The crude product is submitted to silica gel chromatography using a mixture of THF/Et$_3$N (50/2) as solvent, obtaining 0.07 g (35%) of the title product.

EXAMPLE 9

4-(N-isobutylamino)-5,6-dihydro-4H-thien-(2,3-b)-thiopyran-2-sulfonamide-7,7-dioxide

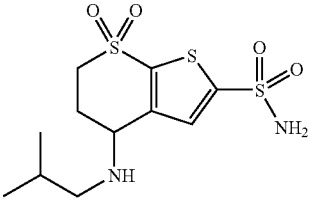

This is prepared following the process of Example 8a, from 0.6 g (0.0015 mol) of 4-(N-acetyl-N-isobutylamino)-5,6-dihydro-4H-thien-(2,3-b)-thiopyran-7,7-dioxide. The crude product is submitted to silica gel chromatography using a mixture of THF/Et$_3$N (50/2) as solvent, obtaining 0.28 g (52%) of the title product.

EXAMPLE 10

(4S-trans)-4-(N-ethylamino)-5,6-dihydro-6-methyl-4H-thien-(2,3-b)-thiopyran-2-sulfonamide-7,7-dioxide Hydrochloride

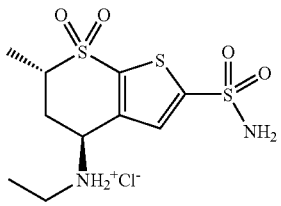

0.55 g (0.0017 mol) of (4S-trans)-4-(N-ethylamino)-5,6-dihydro-6-methyl-4H-thien-(2,3-b)-thiopyran-2-sulfonamide-7,7-dioxide are dissolved in 25 ml of ethyl acetate, and the pH is set to 1 with hydrochloric acid. The crude product

EXAMPLE 11

4-(N-isobutylamino)-5,6-dihydro-4H-thien-(2,3-b)-thiopyran-2-sulfonamide-7,7-dioxide Hydrochloride

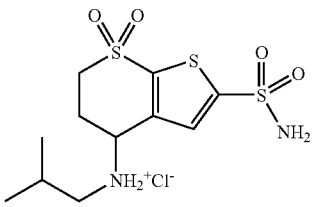

This is prepared following the process of Example 10 from 0.28 g ($8\times10^{-4}$ mol) of 4-(N-acetyl-N-isobutylamino)-5,6-dihydro-4H-thien-(2,3-b)-thiopyran-7,7-dioxide, obtaining 0.28 g (91%) of the title product.

What is claimed is:

1. A process for obtaining 4-(N-alkylamino)-5,6-dihydro-4H-thien-(2,3-b)-thiopyran-2-sulfonamide-7,7-dioxides of general formula (I)

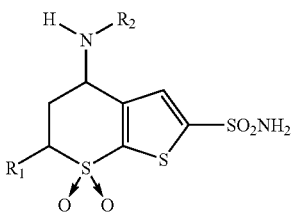
(I)

wherein
$R_1$ is H or $C_{1-5}$ alkyl, and
$R_2$ is $C_{1-5}$ alkyl,
their individual cis or trans diastereomers, their individual levo or dextro enantiomers, or isomeric mixtures thereof, and pharmaceutically acceptable salts thereof, which comprises a) protecting the nitrogen present in the aminosulfone of formula (II)

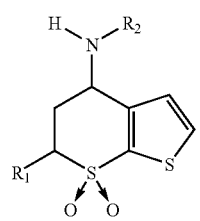
(II)

wherein $R_1$ and $R_2$ have been defined earlier, with a nitrogen protecting group to obtain an N-protected aminosulfone of formula (III)

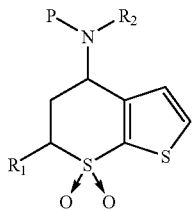
(III)

wherein $R_1$ and $R_2$ are as previously defined and P is a nitrogen protecting group;

b) introducing a sulfonamide group at position 2 of said N-protected aminosulfone (III) to obtain the sulfonamide intermediate of formula (VI)

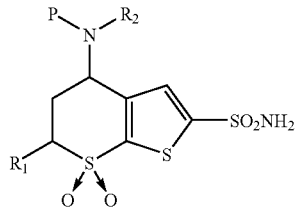
(VI)

wherein $R_1$ and $R_2$ are as previously defined and P is a nitrogen protecting group; and c) eliminating the nitrogen protecting group to obtain the compound of formula (I).

2. Process according to claim 1, in which said nitrogen protecting group (P) is selected from an amide, a carbamate, a sulfonamide and a benzyl derivative.

3. Process according to claim 1, in which said nitrogen protecting group (P) is acetamide.

4. Process according to claim 1, in which in said aminosulfone (II), $R_1$ is $C_{1-5}$ alkyl, $R_2$ is $C_{1-5}$ alkyl, the stereochemical relation between $R_1$ and $R_2$ is trans and the chirality is 4S, 6S.

5. Process according to claim 4, in which in said aminosulfone (II), $R_1$ is methyl, $R_2$ is ethyl, the stereochemical relation between $R_1$ and $R_2$ is trans and the chirality is 4S, 6S.

6. Process according to claim 1, in which in said aminosulfone (II), $R_1$ is hydrogen, $R_2$ is isobutyl, and the chirality is 4S.

7. Process according to claim 1, in which in said aminosulfone (II) is a racemic mixture of 4-(N—$C_{1-5}$ alkyl)-amino-5,6-dihydro-4H-thien-(2,3-b)-thiopyran-7,7-dioxide.

8. Process according to claim 1, in which in said aminosulfone (II) is a racemic mixture of trans-4-(N—$C_{1-5}$ alkyl)-amino-5,6-dihydro-6-($C_{1-5}$ alkyl)-4H-thien-(2,3-b)-thiopyran-7,7-dioxide.

9. Process according to claim 1, in which the introduction of said sulfonamide group at position 2 of the N-protected aminosulfone (III) to obtain the sulfonamidated intermediate of formula (VI) comprises the stages of:

i) sulfonylation of said compound (III) to obtain the sulfonylated intermediate of formula (IV)

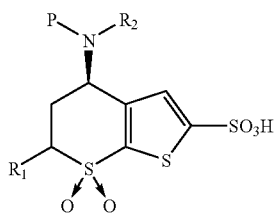

wherein
R₁ is H or $C_{1-5}$ alkyl,
R₂ is $C_{1-5}$ alkyl, and
P is a nitrogen protecting group;
ii) chloration of said compound (IV) to obtain the sulfonylated intermediate of formula (V)

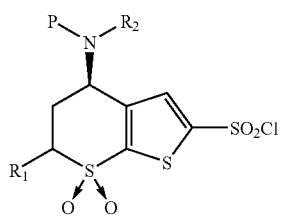

wherein R₁, R₂ and P are as defined earlier; and
iii) sulfonamidation of said compound (V) to obtain said sulfonamidated intermediate of formula (VI).

10. Process according to claim 9, in which the sulfonylation of the N-protected amino sulfone (III) is performed by addition thereto of chlorosulfonic acid at a temperature comprised between −10° C. and +5° C., followed by heating to a temperature comprised between 20° C. and 50° C.

11. Process according to claim 9, in which the chloration of (IV) is carried out by addition of thionyl chloride to said intermediate (IV), at a temperature comprised between −5° C. and +30° C., followed by heating at a temperature comprised between 20° C. and 50° C.

12. Process according to claim 9, in which the formation of sulfonamide (VI) is carried out by addition of a mixture of THF/aqueous ammonia to the intermediate (V), at a temperature comprised between −5° C. and +10° C., followed by neutralisation of the reaction mixture, elimination of the organic solvent and isolation of said compound (VI).

13. Process according to claim 1, in which in the compound (I), R₁ is $C_{1-5}$ alkyl, R₂ is $C_{1-5}$ alkyl, the stereochemical relation between R₁ and R₂ is trans and the chirality is 4S, 6S.

14. Process according to claim 1, in which in compound (I), R₁ is methyl, R₂ is ethyl, the stereochemical relation between R₁ and R₂ is trans and the chirality is 4S, 6S.

15. Process according to claim 1, in which in the compound (I), R₁ is hydrogen, R₂ is isobutyl and the chirality is 4S.

16. Process according to claim 1, in which compound (I) is a racemic mixture of enantiomers and comprises, in addition, resolution of said mixture to separate at least one of the enantiomers of said racemic mixture.

17. Process for the enantioselective synthesis of an enantiomer of a 4-(N—($C_{1-5}$ alkyl)amino)-5,6-dihydro-4H-thien-(2,3-b)-thiopyran-2-sulfonamide-7,7-dioxide from the corresponding 4-(N—$C_{1-5}$ alkyl)amino-5,6-dihydro-4H-thien-(2,3-b)-thiopyran-7,7-dioxide with the appropriate chirality, which comprises protecting the alkylamino group, introducing the sulfonamide group and releasing the protecting group, according to stages a), b) and c) of the process of claim 1.

18. Process for the enantioselective synthesis of (4S)-4-(N—($C_{1-5}$ alkyl)amino-5,6-dihydro-4H-thien-(2,3-b)-thiopyran-2-sulfonamide-7,7-dioxide from the corresponding (4S)-4-(N—$C_{1-5}$ alkyl)amino-5,6-dihydro-4H-thien-(2,3-b)-thiopyran-7,7-dioxide, which comprises protecting the alkylamino group, introducing the sulfonamide group and releasing the protecting group, according to stages a), b) and c) of the process of claim 1.

19. Process for the enantioselective synthesis of (4S-trans)-4-(N—$C_{1-5}$ alkyl)amino-5,6-dihydro-(6S)-($C_{1-5}$ alkyl)-4H-thien-(2,3-b)-thiopyran-2-sulfonamide-7,7-dioxide from the corresponding (4S-trans)-4-(N—$C_{1-5}$ alkyl)amino-5,6-dihydro-(6S)-($C_{1-5}$ alkyl)-4H-thien-(2,3-b)-thiopyran-7,7-dioxide, which comprises protecting the alkylamino group, introducing the sulfonamide group and releasing the protecting group, according to stages a), b) and c) of the process of claim 1.

20. An intermediate of general formula (III)

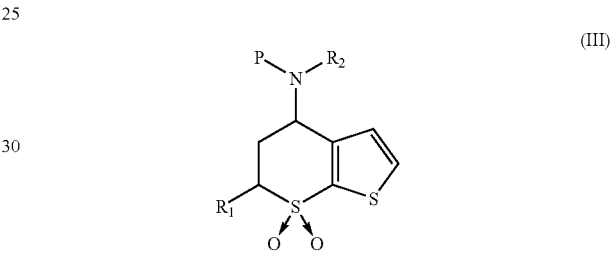

wherein
R₁ is H or $C_{1-5}$ alkyl,
R₂ is $C_{1-5}$ alkyl, and
P is a nitrogen protecting group;
its individual cis or trans diastereomers, its individual levo or dextro enantiomers, or isomeric mixtures thereof.

21. Compound according to claim 20, selected from:
4-(N-acetyl-N-ethylamino)-5,6-dihydro-6-methyl-4H-thien-(2,3-b)-thiopyran-7,7-dioxide, its individual cis or trans diastereomers, its individual levo or dextro enantiomers, or isomeric mixtures thereof; and
4-(N-acetyl-N-isobutylamino)-5,6-dihydro-4H-thien-(2,3-b)-thiopyran-2-7,7-dioxide, its individual cis or trans diastereomers, its individual levo or dextro enantiomers, or isomeric mixtures thereof.

22. An intermediate of general formula (IV)

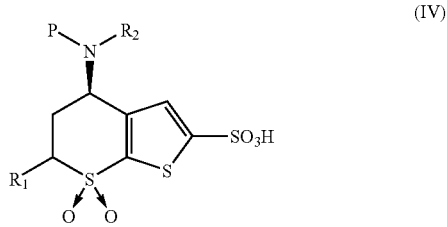

wherein
R₁ is H or $C_{1-5}$ alkyl,
R₂ is $C_{1-5}$ alkyl, and
P is a nitrogen protecting group;

its individual cis or trans diastereomers, its individual levo or dextro enantiomers, or isomeric mixtures thereof.

23. Compound according to claim 22, selected from:
4-(N-acetyl-N-ethylamino)-5,6-dihydro-6-methyl-4H-thien-(2,3-b)-thiopyran-7,7-dioxide 2-sulfonic acid, its individual cis or trans diastereomers, its individual levo or dextro enantiomers, or isomeric mixtures thereof; and
4-(N-acetyl-N-isobutylamino)-5,6-dihydro-4H-thien-(2,3-b)-thiopyran-7,7-dioxide 2-sulfonic acid, its individual cis or trans diastereomers, its individual levo or dextro enantiomers, or isomeric mixtures thereof.

24. An intermediate of general formula (V)

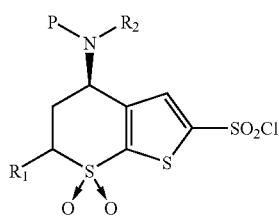

(V)

wherein
$R_1$ is H or $C_{1-5}$ alkyl,
$R_2$ is $C_{1-5}$ alkyl, and
P is a nitrogen protecting group;
its individual cis or trans diastereomers, its individual levo or dextro enantiomers, or isomeric mixtures thereof.

25. Compound according to claim 24, selected from:
4-(N-acetyl-N-ethylamino)-5,6-dihydro-6-methyl-4H-thien-(2,3-b)-thiopyran-7,7-dioxide 2-sulfonic acid chloride, its individual cis or trans diastereomers, its individual levo or dextro enantiomers, or isomeric mixtures thereof; and
4-(N-acetyl-N-isobutylamino)-5,6-dihydro-4H-thien-(2,3-b)-thiopyran-7,7-dioxide 2-sulfonic acid chloride, its individual cis or trans diastereomers, its individual levo or dextro enantiomers, or isomeric mixtures thereof.

26. An intermediate of general formula (VI)

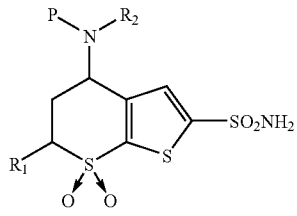

(VI)

wherein
$R_1$ is H or $C_{1-5}$ alkyl,
$R_2$ is $C_{1-5}$ alkyl, and
P is a nitrogen protecting group;
its individual cis or trans diastereomers, its individual levo or dextro enantiomers, or isomeric mixtures thereof.

27. Compound according to claim 26, selected from:
4-(N-acetyl-N-ethylamino)-5,6-dihydro-6-methyl-4H-thien-(2,3-b)-thiopyran-7,7-dioxide 2-sulfonamide, its individual cis or trans diastereomers, its individual levo or dextro enantiomers, or isomeric mixtures thereof; and
4-(N-acetyl-N-isobutylamino)-5,6-dihydro-4H-thien-(2,3-b)-thiopyran-7,7-dioxide 2-sulfonamide, its individual cis or trans diastereomers, its individual levo or dextro enantiomers, or isomeric mixtures thereof.

28. A chiral aminosulfone selected from the group consisting of:
i) (4S-trans)-4-(N-alkylamino)-5,6-dihydro-6-alkyl-4H-thien-(2,3-b)-thiopyran-7,7-dioxide (IIa)

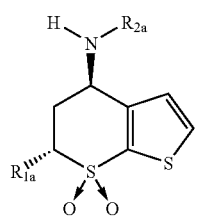

(IIa)

wherein
$R_{1a}$ and $R_{2a}$, independently, are $C_{1-5}$ alkyl, and
ii) (4S)-(N-alkylamino)-5,6-dihydro-4H-thien-(2,3-b)-thiopyran-7,7-dioxide (IIb)

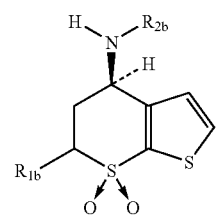

(IIb)

wherein
$R_{1b}$ is H, and
$R_{2b}$ is $C_{1-5}$ alkyl.

29. Compound according to claim 28, selected from:
(4S-trans)-4-(N-ethylamino)-5,6-dihydro-6-methyl-4H-thien-(2,3-b)-thiopyran-7,7-dioxide, and
(4S)-4-(N-isobutylamino)-5,6-dihydro-4H-thien-(2,3-b)-thiopyran-7,7-dioxide.

* * * * *